(12) United States Patent
Yoo

(10) Patent No.: US 6,835,174 B2
(45) Date of Patent: Dec. 28, 2004

US006835174B2

(54) ACUPRESSURE DEVICE FOR FINGERS

(75) Inventor: Tae-woo Yoo, Seoul (KR)

(73) Assignee: Dong-hoon Yoo, Seoul (KR)

( * ) Notice: Subject to any disclaimer, the term of this patent is extended or adjusted under 35 U.S.C. 154(b) by 316 days.

(21) Appl. No.: 10/077,356

(22) Filed: Feb. 15, 2002

(65) Prior Publication Data

US 2003/0045899 A1 Mar. 6, 2003

(30) Foreign Application Priority Data

Sep. 5, 2001 (KR) ........................................ 2001-27158

(51) Int. Cl.$^{7}$ ................................................ A61B 17/00

(52) U.S. Cl. ....................................................... 600/204

(58) Field of Search ................................ 606/204, 207, 606/202, 203

(56) References Cited

FOREIGN PATENT DOCUMENTS

| | | |
|---|---|---|
| KR | 135974 | 1/1993 |
| KR | 300256331 | 2/2000 |
| KR | 200254040 | 11/2001 |

*Primary Examiner*—Vy Q. Bui
(74) *Attorney, Agent, or Firm*—Richard M. Goldberg

(57) ABSTRACT

An acupressure device for fingers includes an inserting unit having an open end for receiving the end of a finger, a cut section in a center of the open end of the inserting unit, a semi-circular base unit having a flat outer surface and an inner surface formed with a plurality of protuberances, and two fixing strips at both sides of the semi-circular base unit.

16 Claims, 6 Drawing Sheets

ACUPRESSURE DEVICE FOR FINGERS

BACKGROUND OF THE INVENTION

1. Field of the Invention

The present invention relates to an acupressure device for fingers and more particularly, to an acupressure device for fingers designed for the end of a finger to be inserted into it in order to provide pressure stimulation effects into fingers with protuberances at the inner surface of the device and to enhance blood circulation effects by producing negative(−) [ion] ions.

The inner surface of the acupressure device for fingers according to the present invention is cast into protuberances, and therefore, the protuberances offer pressure stimulation effects into a finger inserted inside a cutting unit of the invention. The outer surface of the present invention is made into a flat surface, so that there is no space where dirt sticks inside.

Further, the acupressure device for fingers has a control over the inner space according to the thickness of the fingers of the users, since a fixing strip on the front side of the acupressure device can be pressured hard or slightly.

2. Description of the Prior Art

The prior art of the present invention, Korean Utility Model registration No. 250633, is an acupressure device for fingers made of a board of non-ferrous metals. The inner surface of the prior art is cast into a plurality of protuberances by pressing the outer surface, and therefore, the protuberances of the inner surface provide pressure stimulation effects into a finger inserted inside of it. But the outer surface has a plurality of holes which are made protuberances on the inner side. The holes on the outer surface easily get full of dirt or bacteria.

SUMMARY OF THE INVENTION

The present device was designed to solve the problems described above. Therefore, an object of the present invention is to provide an acupressure device which has a flat outer surface and an inner surface cast with a plurality of protuberances for creating pressure effects to a finger inserted inside the present device. After a user inserts the end of a finger inside an inserting unit and the cut section in a center of the inserting unit, the user presses fixing strips at both sides in order to fit the device to the finger firmly. The protuberances of the inner surface of the present invention stimulate and pressure the end of the finger.

The other object of the present invention is to provide an acupressure device for fingers which offers an enhanced blood circulation effect to fingers by creating negative(−) ions, since the present device is made of nonferrous metals.

Another object of the present invention is to provide an acupressure device of which the inner space can be controlled by pressuring the fixing strips at both sides firmly or slightly according to the thickness of users.

Another object of the present invention is to provide an acupressure device for fingers of which the outer surface is designed so flat that there is no space where dirt sticks inside.

BRIEF DESCRIPTION OF THE DRAWINGS

The other objects and features of the present invention will be hereinafter explained in detail with reference to the accompanying drawings, wherein.

DESCRIPTION OF THE PREFERRED EMBODIMENTS

Figure 1:
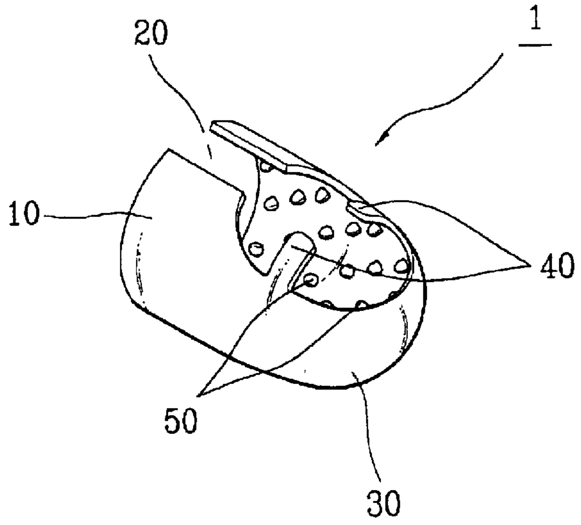
FIG. 1 is a perspective view of the present invention.
Figure 2:
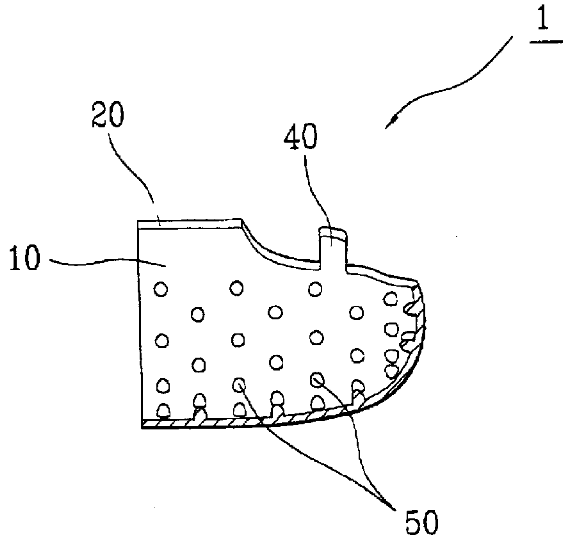
FIG. 2 is a cross-sectional view of the present invention.

The present invention is an acupressure device for fingers 1 including an inserting unit 10 at one side, a cut section 20 in a center of the inserting unit 10, a semi-circular base unit 30 having a flat outer surface and an inner surface cast into a plurality of protuberances 50 at another side, and two fixing strips 40 at both sides of the semi-circular base unit 30.

Numerals 100 and 200 refer to a finger and a fingernail, respectively.

The acupressure device for fingers 1 has a flat outer surface and an inner surface cast into a plurality of protuberances 50 for creating pressure stimulating effects to a finger inserted inside the inserting unit 10.

Figure 3:
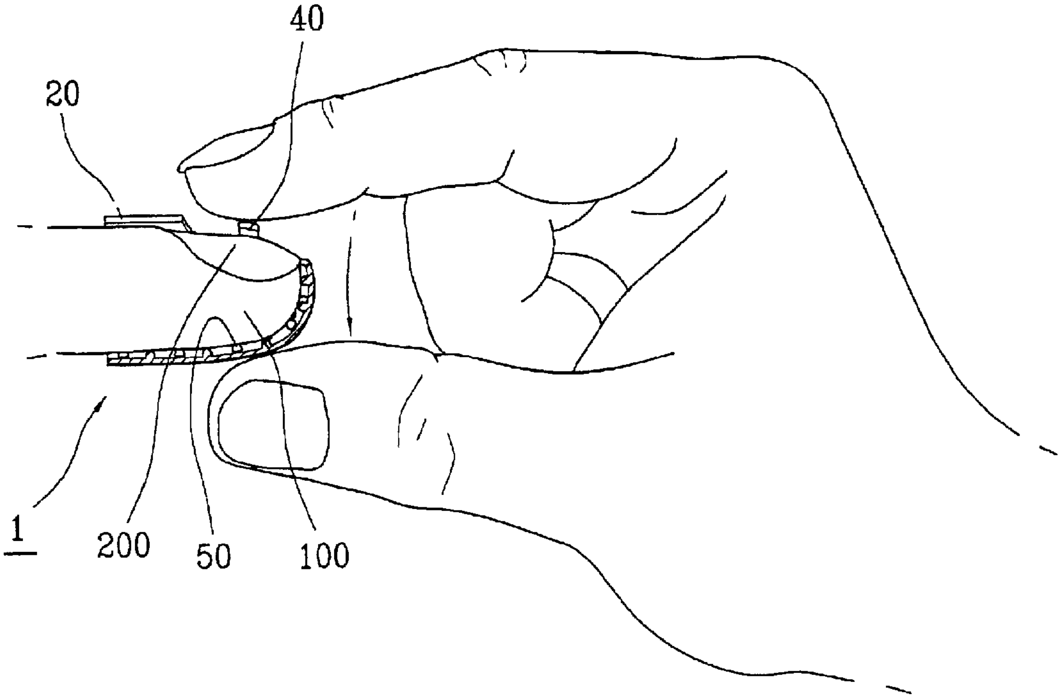
FIG. 3 shows an example of a state before pressuring fixing strips after wearing the present invention.
Figure 4:
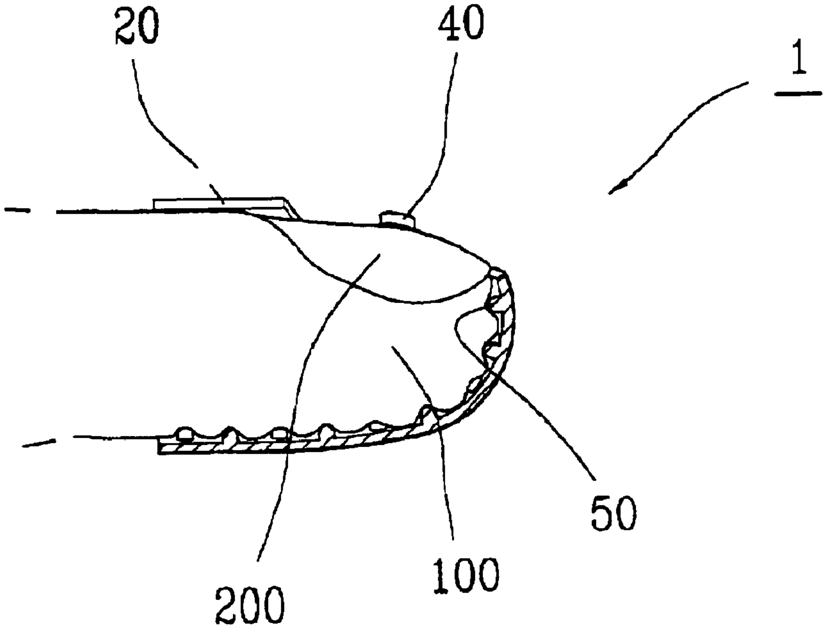
FIG. 4 is a cross-sectional view showing a state of wearing the present invention.
Figure 5:
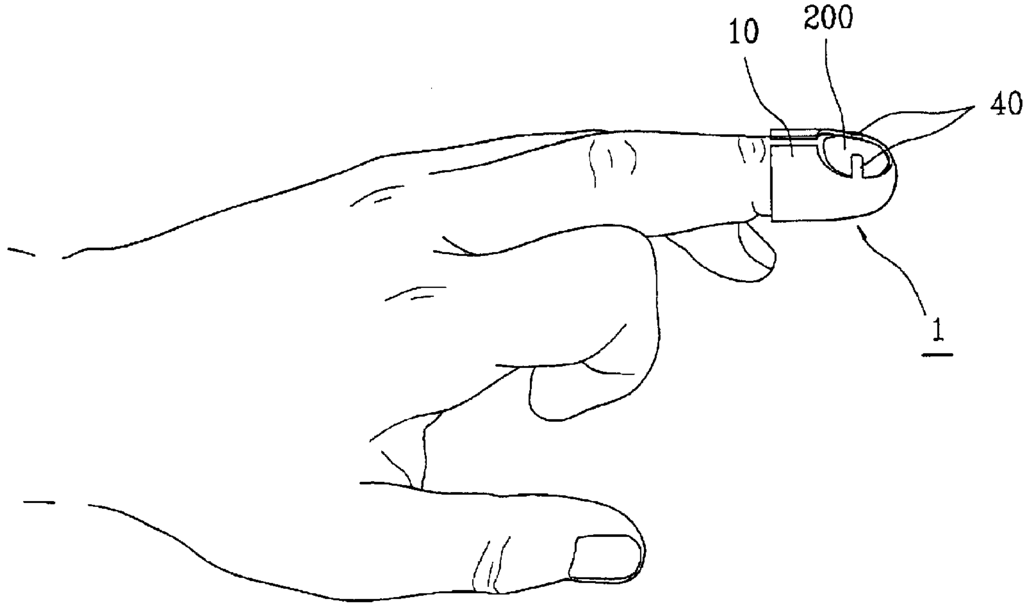
FIG. 5 is a perspective view showing a state of wearing the present invention.

As shown in FIG. 3 and FIG. 4, a finger 100 is inserted in an inserting unit 10 and the cut section 20 in a center of the acupressure device for fingers 1 and then the fixing strips 40 at both sides are pressured firmly or slightly according to the thickness of the finger 100 to fit the present device to the finger 100 firmly. And then the protuberances 50 of the inner surface of the acupressure device for fingers 1 stimulate and pressure the finger 100.

After finishing massaging the finger 100, users can easily pull out the acupressure device for fingers 1 by reiterating just simply the above process of wearing the present device in an opposite order. In other words, a user spreads both fixing strips 40 from the finger 100 first, and then spreads the cut section 20, and draws the finger 100 from the present device 1.

Figure 6:
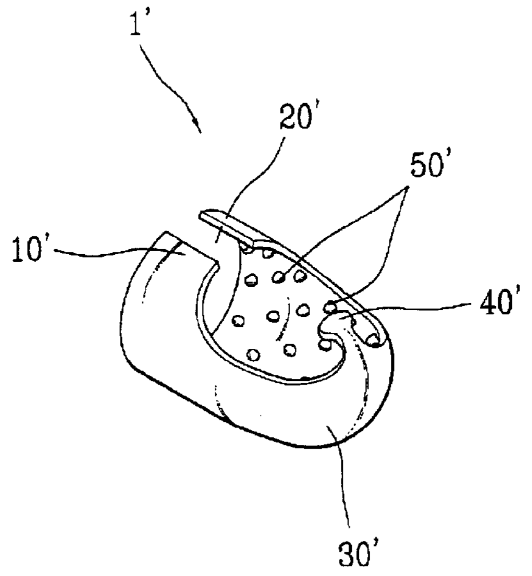
FIG. 6 is a perspective view of another embodiment of the present invention.
Figure 7:
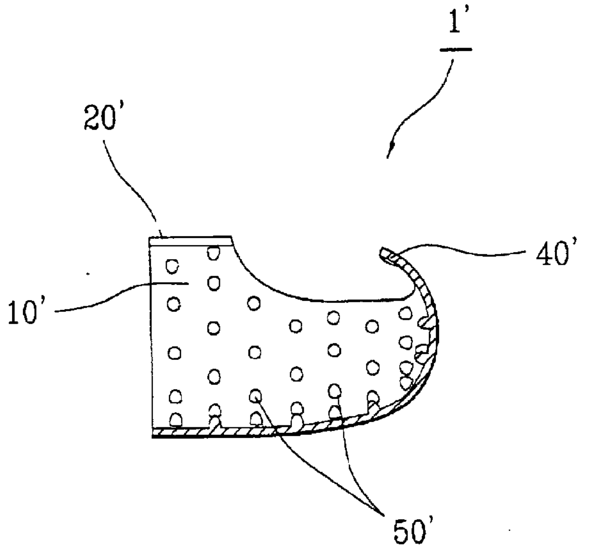
FIG. 7 is a cross-sectional view of the FIG. 6.
Figure 8:
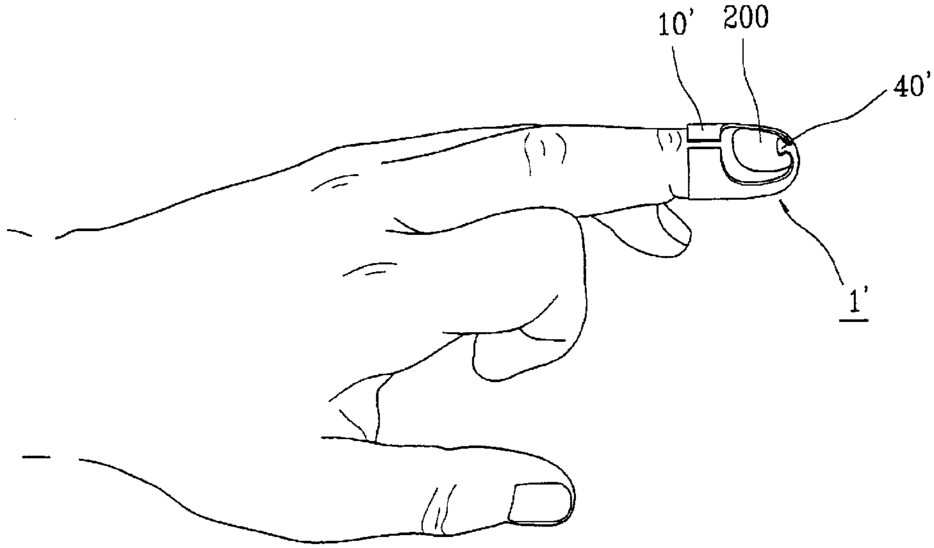
FIG. 8 is a perspective view showing a state of wearing the present invention.

As shown in FIG. 6, an acupressure device for fingers 1' according to another embodiment of the present invention includes a cut section 20' in a center of an inserting unit 10', a fixing strip 40' at the upper central side of a semi-circular base unit 30', a flat outer surface and an inner surface cast into a plurality of protuberances 50'.

A finger 100 is inserted inside the inserting unit 10' and the cut section 20' in a center of the acupressure device 1' for fingers. The fixing strips 40' in the upper central side of the acupressure device for fingers 1' are pressured firmly or slightly according to the thickness of the finger 100 to fit the present device to the finger 100 firmly. And then the protuberances 50' of the inner surface of the acupressure device for fingers 1' stimulate and pressure the finger 100.

What is claimed is:

1. An acupressure device for fingers comprising:

an inserting unit having an opening at one end for receiving an end of a finger, a cut section in a center of said inserting unit at said one end, a semi-circular base unit at an opposite end and having a flat outer surface and an inner surface formed with a plurality of protuberances, and at least one fixing strip at said semi-circular base unit, said acupressure device have an overall length which, when assembled on a finger, is insufficient to cover a first distal joint of the finger, thereby enabling a full range of bending of the finger.

2. An acupressure device for fingers according to claim 1, wherein said at least one fixing strip includes a fixing strip at an upper central side of said semi-circular base unit.

3. An acupressure device for fingers according to claim 1, wherein said at least one fixing strip includes two fixing strips at opposite sides of said semi-circular base unit.

4. An acupressure device for fingers according to claim 1, wherein said two fixing strips face each other.

5. An acupressure device for fingers according to claim 1, further comprising an outer surface which is smooth and free of recesses at positions corresponding to said protuberances.

6. An acupressure device for fingers according to claim 1, wherein:

the semi-circular base unit has an open area at an upper end thereof for receiving a nail of the finger, and the at least one fixing strip extends into said open area at a position above the nail when the acupressure device is inserted on the finger, the at least one fixing strip having a distal end that terminates at the nail when the acupressure device is inserted on the finger so as to be pressed onto and secured to the nail with a desired tightness, in order to secure the acupressure device to the finger.

7. An acupressure device for fingers comprising:

an inserting unit having an opening at one end for receiving an end of a finger, a cut section in a center of said inserting unit at said one end, a semi-circular base unit at an opposite end and having a flat outer surface and an inner surface formed with a plurality of protuberances, at least one fixing strip at said semi-circular base unit, and an outer surface which is smooth and free of recesses at positions corresponding to said protuberances.

8. An acupressure device for fingers according to claim 7, wherein said at least one fixing strip includes a fixing strip at an upper central side of said semi-circular base unit.

9. An acupressure device for fingers according to claim 7, wherein said at least one fixing strip includes two fixing strips at opposite sides of said semi-circular base unit.

10. An acupressure device for fingers according to claim 7, wherein said two fixing strips face each other.

11. An acupressure device for fingers according to claim 7, wherein:

the semi-circular base unit has an open area at an upper end thereof for receiving a nail of the finger, and the at least one fixing strip extends into said open area at a position above the nail when the acupressure device is inserted on the finger, the at least one fixing strip having a distal end that terminates at the nail when the acupressure device is inserted on the finger so as to be pressed onto and secured to the nail with a desired tightness, in order to secure the acupressure device to the finger.

12. An acupressure device for fingers comprising:

an inserting unit having an opening at one end for receiving an end of a finger, a cut section in a center of said inserting unit at said one end, a semi-circular base unit at an opposite end and having a flat outer surface and an inner surface formed with a plurality of protuberances, the semi-circular base unit having an open area at an upper end thereof for receiving a nail of the finger, and at least one fixing strip at said semi-circular base unit and extending into said open area at a position above the nail when the acupressure device is inserted on the finger, the at least one fixing strip having a distal and that terminates at the nail when the acupressure device is inserted on the finger so as to be pressed onto and secured to the nail with a desired tightness, in order to secure the acupressure device to the finger.

13. An acupressure device for fingers according to claim 12, wherein said at least one fixing strip includes a fixing strip at an upper central side of said semi-circular base unit.

14. An acupressure device for fingers according to claim 12, wherein said at least one fixing strip includes two fixing strips at opposite sides of said semi-circular base unit.

15. An acupressure device for fingers according to claim 12, wherein said two fixing strips face each other.

16. An acupressure device for fingers according to claim 12, wherein:

said acupressure device have an overall length which, when assembled on a finger, is insufficient to cover a first distal joint of the finger, thereby enabling a full range of bending of the finger, and said acupressure device has an outer surface which is smooth and free of recesses at positions corresponding to said protuberances.

* * * * *